United States Patent
Takasugi et al.

[11] Patent Number: 5,550,582
[45] Date of Patent: Aug. 27, 1996

[54] ENDOSCOPE-IMAGE PROCESSING APPARATUS FOR PERFORMING IMAGE PROCESSING OF EMPHASIS IN ENDOSCOPE IMAGE BY PIGMENT CONCENTRATION DISTRIBUTION

[75] Inventors: Kei Takasugi, Hachioji; Kazunari Nakamura, Hino, both of Japan

[73] Assignee: Olympus Optical Co., Ltd., Tokyo, Japan

[21] Appl. No.: 175,242

[22] Filed: Dec. 29, 1993

[30] Foreign Application Priority Data

Mar. 19, 1993 [JP] Japan ............................ 5-060631
Mar. 30, 1993 [JP] Japan ............................ 5-072471

[51] Int. Cl.⁶ ........................... H04N 9/64; H04N 7/18
[52] U.S. Cl. ........................... 348/65; 348/66; 348/67; 348/68; 348/29
[58] Field of Search ........................... 348/29, 65, 67, 348/28

[56] References Cited

U.S. PATENT DOCUMENTS

| | | | |
|---|---|---|---|
| 4,914,512 | 4/1990 | Sekiguchi | 348/29 |
| 4,961,110 | 10/1990 | Nakamura | 348/67 |
| 4,998,973 | 3/1991 | Kikuchi | 348/29 |
| 5,034,888 | 7/1991 | Uehara et al. | 348/29 |
| 5,045,935 | 9/1991 | Kikuchi | 348/67 |
| 5,092,331 | 3/1992 | Nakamura et al. | 348/65 |
| 5,111,281 | 5/1992 | Sekiguchi | 348/67 |

FOREIGN PATENT DOCUMENTS

| | | |
|---|---|---|
| 62-266028 | 11/1987 | Japan . |
| 63-54144 | 3/1988 | Japan . |
| 63-173182 | 7/1988 | Japan . |
| 1-185243 | 7/1989 | Japan . |
| 1-223931 | 9/1989 | Japan . |
| 2-224635 | 9/1990 | Japan . |
| 5-3295 | 1/1993 | Japan . |

Primary Examiner—Tommy P. Chin
Assistant Examiner—Anand S. Rao
Attorney, Agent, or Firm—Armstrong, Westerman, Hattori, McLeland & Naughton

[57] ABSTRACT

In an endoscope apparatus, an image processing unit for an endoscope, and a method of emphasizing an endoscope image, conversion processing is performed in which an amount of pigment, such as a hemoglobin pigment, is calculated from the endoscope image which is detected by the use of the endoscope, by a pigment calculating circuit. The amount of pigment is substituted for an amount of pigment in which an amount of shift from a value such as average of the amount of pigment is enlarged, and the amount of pigment is returned to the endoscope image having an amount of pigment in which the amount of shift from an average is enlarged, whereby tone of most parts having the amount of pigment of the average is not changed to an original endoscope image, but the endoscope image in which tone of a portion having the amount of pigment which is shifted from the average is emphasized is generated.

22 Claims, 8 Drawing Sheets

ENDOSCOPE-IMAGE PROCESSING APPARATUS FOR PERFORMING IMAGE PROCESSING OF EMPHASIS IN ENDOSCOPE IMAGE BY PIGMENT CONCENTRATION DISTRIBUTION

BACKGROUND OF THE INVENTION

1. Field of the Invention

The present invention relates to an endoscope-image processing apparatus for performing image processing, which emphasizes an endoscope image which is detected in a visible region, on the basis of a signal of pigment concentration distribution which is calculated by pigment-amount calculation means, to produce the endoscope image, which is provided with ordinary characteristics of the endoscope image and characteristics of the pigment concentration distribution.

2. Description of the Related Art

In recent years, an endoscope in which medical treatment, can be performed without excision by the fact that a body cavity of a patient is observed and a treatment tool is used as occasion demands has widely been used in a medical field.

Further, there is a case where image processing is performed with respect to an endoscope image which is produced by an endoscope, whereby image processing is applied to facilitate discrimination of a normal part or a lesion part.

Regarding the endoscope image, as a prior art which discloses image processing, there is known a method in which RGB images are converted into hue, saturation and brightness and, thereafter, emphasis processing is performed, as disclosed in Japanese Patent Laid-Open No. SHO 62-266028. A method in which histograms of respective hue, saturation and brightness are elongated and are moved, is disclosed in Japanese Patent Laid-Open No. SHO 63-54144. A method in which a quantity of hemoglobin is calculated to perform imaging, is disclosed in Japanese Patent Publication No. HEI 5-3295.

Moreover, as disclosed in Japanese Patent Laid-Open No. HEI 2-224635, processing in which a difference between images which are separated in color from each other is taken to perform emphasis processing on the basis of information thereof is performed.

However, the processing method disclosed in each of Japanese Patent Laid-Open No. SHO 62-266028 and Japanese Patent Laid-Open No. SHO 63-54144 aims at emphasis processing which is matched to a visual sense of a human being. Accordingly, in a case, for example, where color emphasis is performed, a change of delicate color is emphasized. Therefore, contrast is too strong, and an image is inadequate to perform observation for a long period of time.

Furthermore, in the method in which the quantity of hemoglobin is imaged as disclosed in Japanese Patent Publication No. HEI 5-3295, comparison with an endoscope image which is detected in an ordinary or normal visible region is required. That is, the image is brought to an image in a two-dimensional pattern in which an outline and a stereoscopic structure of an affected or diseased part are unknown. Accordingly, by comparison with an ordinary endoscope image, it becomes necessary and indispensable to perform confirmation of a position and a shape or contour of the affected part or the like. In this case, there is such a drawback that, if both the images cannot simultaneously be displayed, confirmation of the position and the contour becomes difficult.

Meanwhile, in the processing method disclosed in Japanese Patent Laid-Open No. HEI 2-224635, the possibility of producing an image which is provided with organism functional information and characteristics of the ordinary endoscope image cannot be totally denied. However, it becomes very difficult to produce an image which is provided with characteristics suitable for diagnosis.

That is, in the publication, the image emphasis performs multiplication between the color signal and the difference signal substantially in proportion to the quantity of hemoglobin, for example. Accordingly, there are many cases where the characteristics of the normal endoscope image are largely varied or modified by the quantity of hemoglobin. Thus, it is possible to change color of the affected part so as to be conspicuous, for example. However, since the healthy parts are also changed in tone, it becomes difficult to notice an affected part. Thus, the image is not provided with characteristics suitable for diagnosis.

Generally, an image in which it is easy to detect the early stages of a lesion (hereinafter referred to as "an early stage of a lesion") is provided with characteristics slightly different from a condition of a healthy part (hereinafter referred to as "a healthy part") becomes an image which is provided with characteristics suitable for diagnosis. In this case, in order to easily identify the early stages of a lesion, it is desirable that the healthy part is also provided with characteristics which are not substantially changed with the tone of the normal endoscope image.

That is, an image processing unit in which image processing capable of assuring the production of an image which is provided with a tone of a normal endoscope image with respect to most parts and which is provided with characteristics which are conspicuous in deceased lesion parts is performed is adequate for diagnosis.

For this reason, it becomes necessary to improve upon the prior art disclosed in the above-described publications so as to ensure production of the image which is provided with the characteristics of both the images and which is suitable for diagnosis.

SUMMARY OF THE INVENTION

It is an object of the invention to provide an endoscope-image processing apparatus capable of producing an endoscope image provided with characteristics suitable for diagnosis, on the basis of organism functional information such as a hemoglobin pigment and the like.

It is another object of the invention to provide an endoscope-image processing apparatus capable of producing an endoscope image which is provided with characteristics easy to discriminate or identify a lesion part under an initial condition.

According to the invention, there is provided an endoscope-image processing apparatus comprising imaging means for imaging a subject image, pigment-quantity distribution calculating means for producing distribution of at least one pigment quantity from the image produced by said imaging means, and emphasis means for replacing the pigment quantity by a pigment quantity enlarged in a quantity of shift from a reference value and thereafter, transforming the replaced pigment quantity to an endoscope image provided with the substituted pigment quantity to thereby perform emphasis of an image. A value higher than the reference value is substituted for a higher pigment quantity, and a value lower than the reference value is replaced with a lower pigment quantity. Thereafter, the pigment quantity is returned to an endoscope image to produce an endoscope image which has an emphasized image, whereby there is produced an endoscope image which is provided with characteristics of a normal endoscope image and which is characterized in that a lesion part is emphasized as to be conspicuous.

BRIEF DESCRIPTION OF THE DRAWINGS

FIGS. 1 to 8 relate to a first embodiment of the invention, FIG. 1 being a side elevational view showing an entire endoscope apparatus of the first embodiment;

DETAILED DESCRIPTION OF THE PREFERRED EMBODIMENT

A preferred embodiment of the present invention will hereunder be described with reference to the accompanying drawings.

Figure 1:
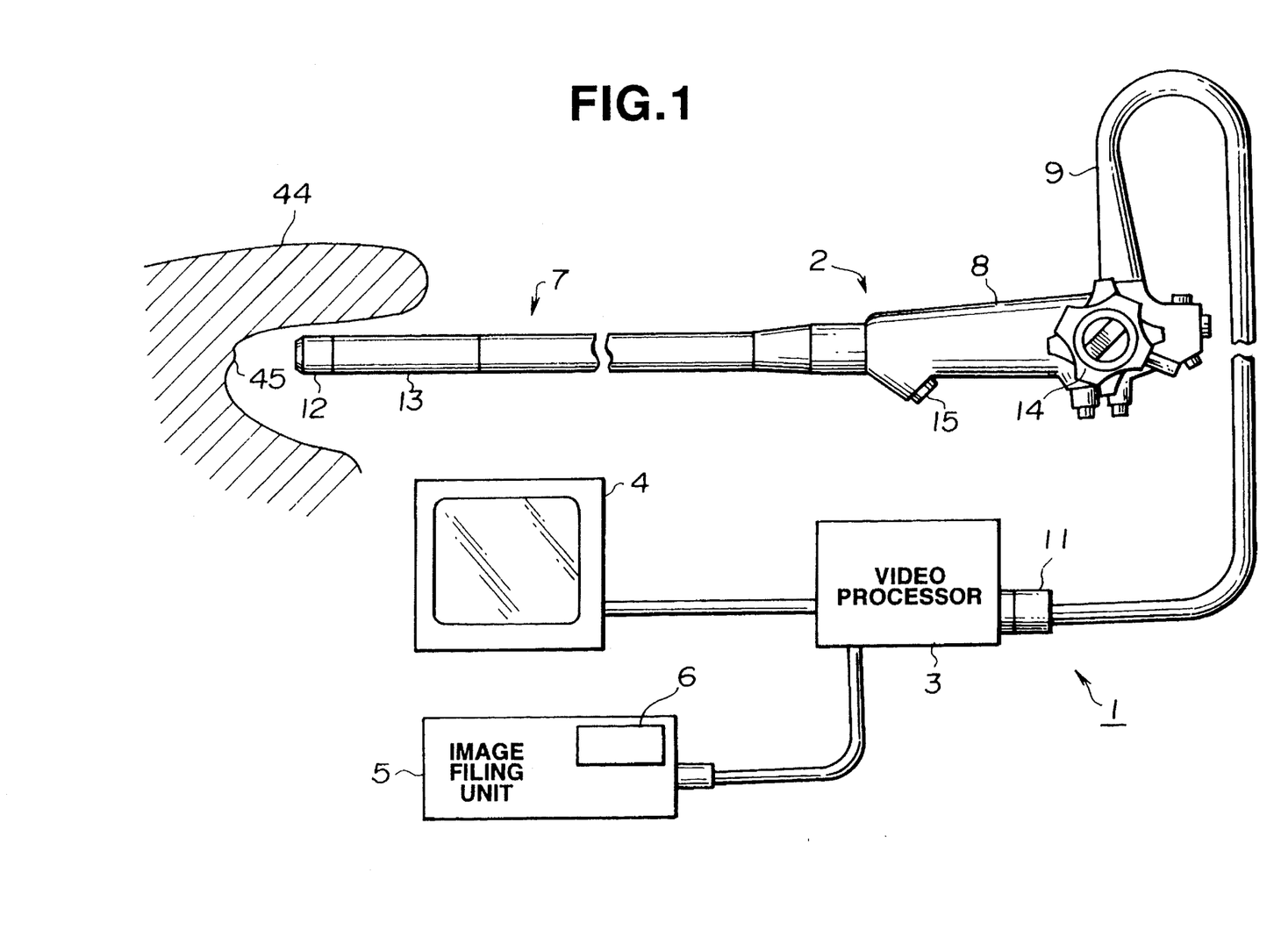

As shown in FIG. 1, and endoscope apparatus 1 provided with the present embodiment comprises an electronic endoscope 2 provided with image pickup means, a video processor 3 for supplying illuminating light to the electronic endoscope 2 and for performing signal processing, a monitor 4 for displaying an image signal which is output from the video processor 3, and an image filling device 5 connected to the video processor 4 for performing image processing and for filing the image. The image filing device 5 includes an image emphasis unit 6 for processing, in emphasis, the image signal which is outputted from the video processor 3.

The electronic endoscope 2 has an inserting section 7 which is, for example, movable and which is elongated. A relatively wide operating section 8 is connected to a rearward end of the inserting section 7. A flexible universal cord 9 extends from a side portion of the operating section 8 on the side of a rearward end thereof. The universal cord 9 has an end thereof which is provided with a connector 11.

A rigid forward end 12 and a curvable curvature portion 13 on the side of a rearward end thereof adjacent to the forward end 12 are successively provided on a forward end of the inserting section 7. Furthermore, a curvature operating knob 14 which is provided on the operating section 8 is operated in angular movement, whereby the curvature portion 13 can be curved both in a lateral direction or in a vertical direction. Moreover, the operating section 8 is provided therein with an inserting port 15 which is in communication with a treatment-tool channel which is provided within the inserting section 7.

Figure 2:
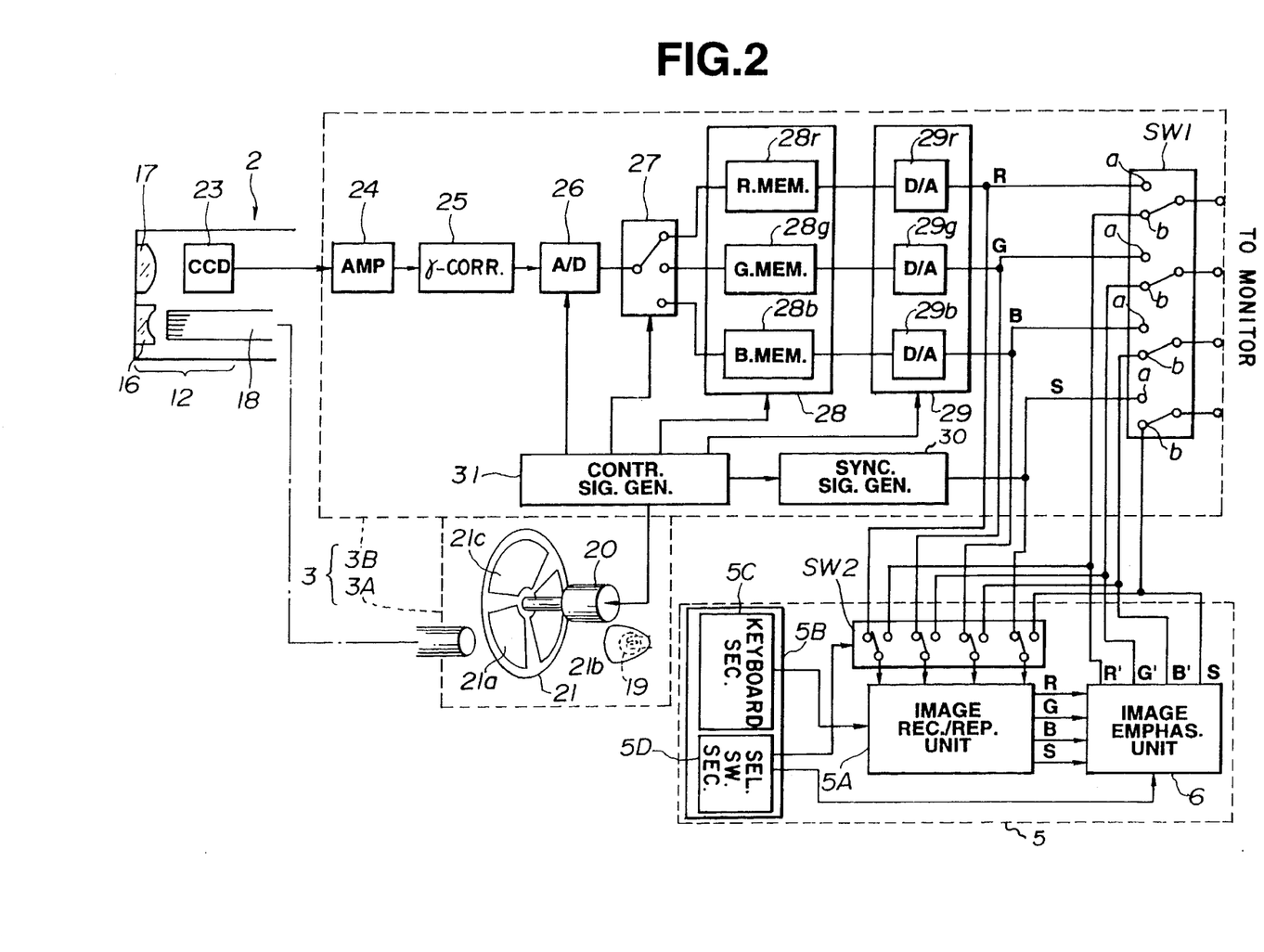
FIG. 2 is a block diagram showing an arrangement of FIG. 1.

As shown in FIG. 2, an illuminating lens 16 and an objective optical system 17 are mounted respectively on an illuminating window and an observing window in the forward end 12. A light guide 18 having a fiber bundle is connected to a rearward side of the illuminating lens 16. The light guide 18 is inserted into the inserting section 7, the operating section 8 and the universal cord 9, and is connected to the connector 11.

The connector 11 is connected to the video processor 3, whereby the arrangement is such that illuminating light which is output from a light source unit 3A within the video processor 3 is input to an incident end of the light guide 18.

The light source unite 3A is provided with a lamp 19, a rotary filter 21 arranged in an illuminating optical path of the lamp 19 and rotated by a motor 20, and the rotary filter 21 and the lamp 19.

Figure 3:
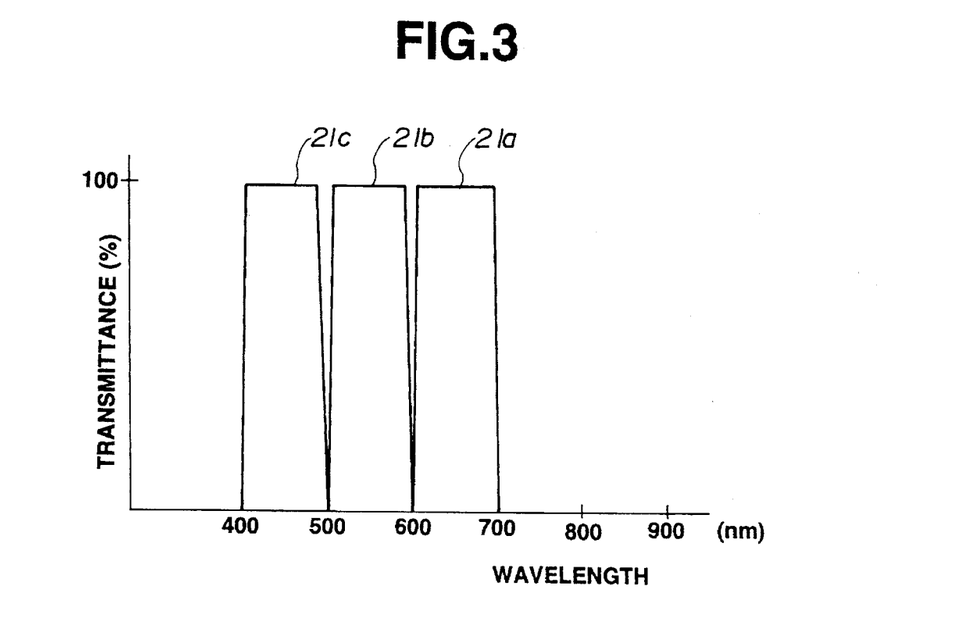
FIG. 3 is a graph showing a transparent characteristic of a color transparent filter.

The lamp 19 outputs light in wavelengths ranging from the ultraviolet to the infrared. Color transparent filters 21a, 21b and 21c for transparentizing lights of wavelength ranges different from each other are arranged on the rotary filter 21 along a peripheral direction. Characteristics of the respective color transparent filters 21a, 21b and 21c arranged on the rotary filter 21 are set to characteristics in which wavelength ranges of respective R, G and B shown in FIG. 3 are transparentized.

The arrangement is such that light which is output from the lamp 19 is separated in a time-series manner into wavelength ranges, by the rotary filter 21, and is incident upon the incident end of the light guide 18. The illuminating light is arranged as to be able to be guided to the forward end 12 by the light guide 18, to pass through the illuminating lens 16 which is mounted on the illuminating window in a forward-end surface, and to be irradiated upon a subject such as a part to be inspected 45.

Meanwhile, a CCD array 23, for example, serving as a solid state image pickup device is arranged on an imaging position of the objective optical system 17. The subject image which is illuminated by the surface-sequential illuminating light is imaged onto a photoelectric conversion surface of the CCD array 23 by the objective optical system 17, and is converted to an electric signal by the CCD array 23. The arrangement is such that the image signal from the CCD array 23 is input into a signal processing circuit 3B, and is input to an amplifier 24 for performing amplification to output an electrical signal within a predetermined range (0~1 volt, for example).

After the output electrical signal of the amplifier 24 has been γ-corrected by a γ correction circuit 25, the output electrical signal of the amplifier 24 is converted to a digital signal by an A/D converter 26, and is input to a selector 27 having a single input and three outputs. RGB signals which are sent in a time series manner are separated into respective R, G and B color signals by the selector 27, and are input to a memory section 28.

The arrangement is such that the separated R, G and B color signals are stored respectively into memories 28r, 28g and 28b of the memory section 28 which correspond respectively to R, G and B color signals. The arrangement is such that the color signals R, G and B which are read out respectively from the memories 28r, 28g and 28b are converted respectively to analog three-primary-color signals R, G and B by D/A converters 29r, 29g and 29b included in D/A converter section 29. The color signals R, G and B pass through a switch SW1 and are respectively output to the monitor 4 from signal output ends of the respective R, G and B D/A converters.

Furthermore, a synchronous signal S from a synchronous-signal generating circuit 30 is output from a synchronous-signal output end thereof, together with the three-primary-color signals R, G and B. The three-primary-color signals R, G and B and the synchronous signal S are output to the monitor 4 through the switch SW1. Further, the three-primary-color signals R, G and B and the synchronous signal S are input to an image recording/reproducing unit 5A through a switch SW2 within the image filing device 5.

Moreover, a control-signal generating portion 31 is provided in the signal processing circuit 3B. The color-signal generating portion 31 sends control signals respectively to the synchronous-signal generating circuit 30 and the motor 20, in addition to control signals which perform control of timing with respect to the conversion operation of the A/D converter 26, changeover or switching of the selector 27, writing/reading-out of the memories 28r, 28g and 28b, and conversion operations of the D/A converters 29r, 29g and 29b.

At the image filing device 5, a file name in a case where recording is performed, from a keyboard portion 5C of a front panel 5B is input whereby endoscope image data are recorded onto the recording/reproducing unit 5A by an assigned file name. Furthermore, in a case where reproduction is indicated, if the file name is input from the keyboard portion 5C, the endoscope image data of the assigned file name are read out and are input to an image emphasis unit 6. In a case where image emphasis is performed by the image emphasis unit 6, indication of an amount of emphasis is performed further from a selective switching portion 5D or the keyboard portion 5C of the front panel 5B. The arrangement can also be such that emphasis is performed by a preset predefined value without performing the indication.

Figure 6:
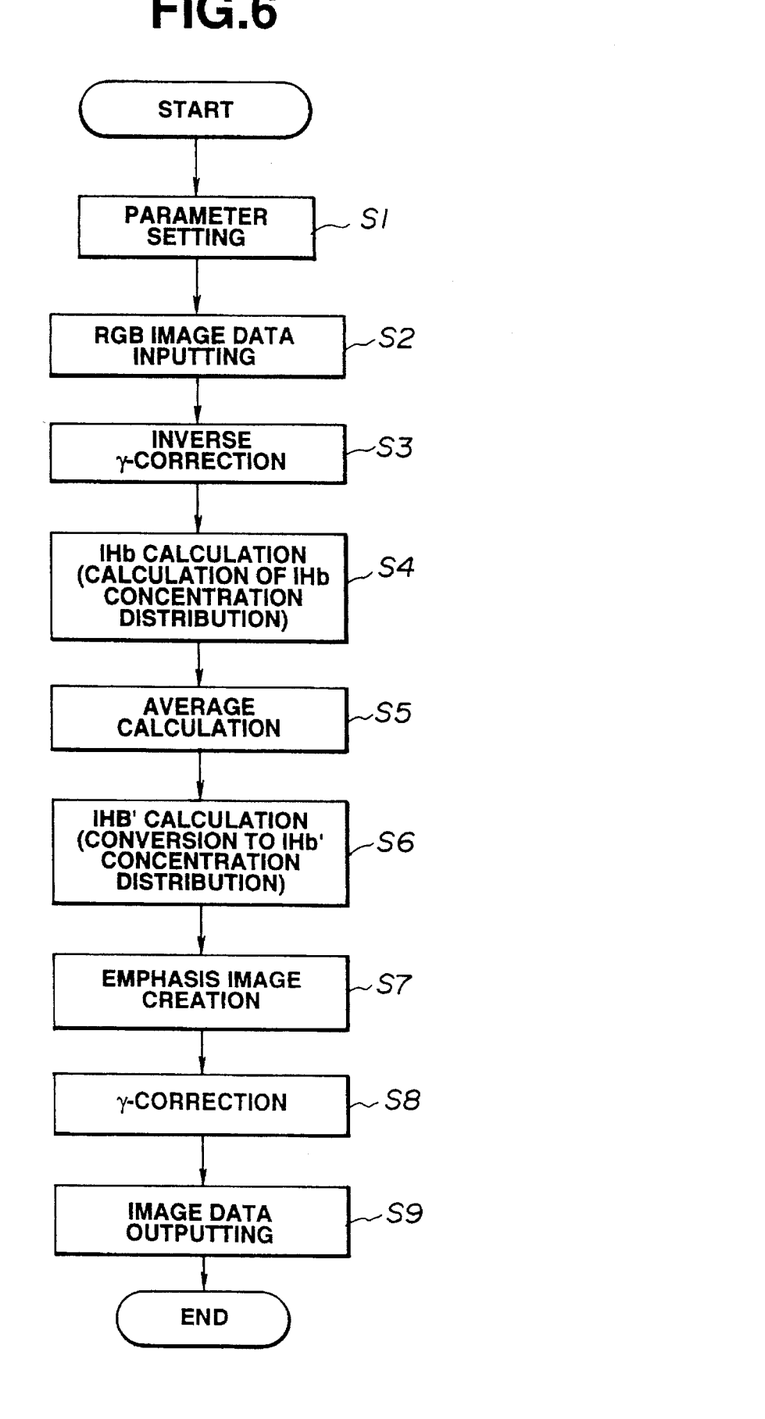
FIG. 6 is a flow chart showing an entire image emphasis method.

Emphasis processing as shown in FIG. 6 is performed by the image emphasis unit 6. The endoscope image data processed in emphasis are recorded on the image recording/reproducing unit 5A through the switch SW2, or are output to the monitor 4 through the switch SW1 of the video processor 3, so that the endoscope image processed in emphasis can be displayed.

The image emphasis unit 6 calculates distribution of an amount of hemoglobin (hereinafter referred simply to as "IHb") as an amount of pigment, with respect to the three-primary-color signals R, G and B which are inputted in synchronism with the synchronous signal. That is, the image emphasis unit 6 calculates distribution of hemoglobin concentration. After the concentration has been processed in emphasis, the concentration is converted to three-primary-color signals R', G' and B', and the image emphasis unit 6 outputs the converted three-primary-color signals R', G' and B' from an output end as a video signal which is processed in emphasis by the amount of hemoglobin, together with the synchronous signal S.

The three-primary-color signals R', G' and B' processed in emphasis are recorded by the image recording/reproducing unit 5A, and are output to the monitor 4 through contacts b of the switch SW1.

Any one of the video signals which is not processed in emphasis and the video signal which is processed in emphasis is inputted to the monitor 4 by selection of the switch SW1. A corresponding unemphasized or emphasized endoscope image is displayed by the input video signal.

Figure 4:
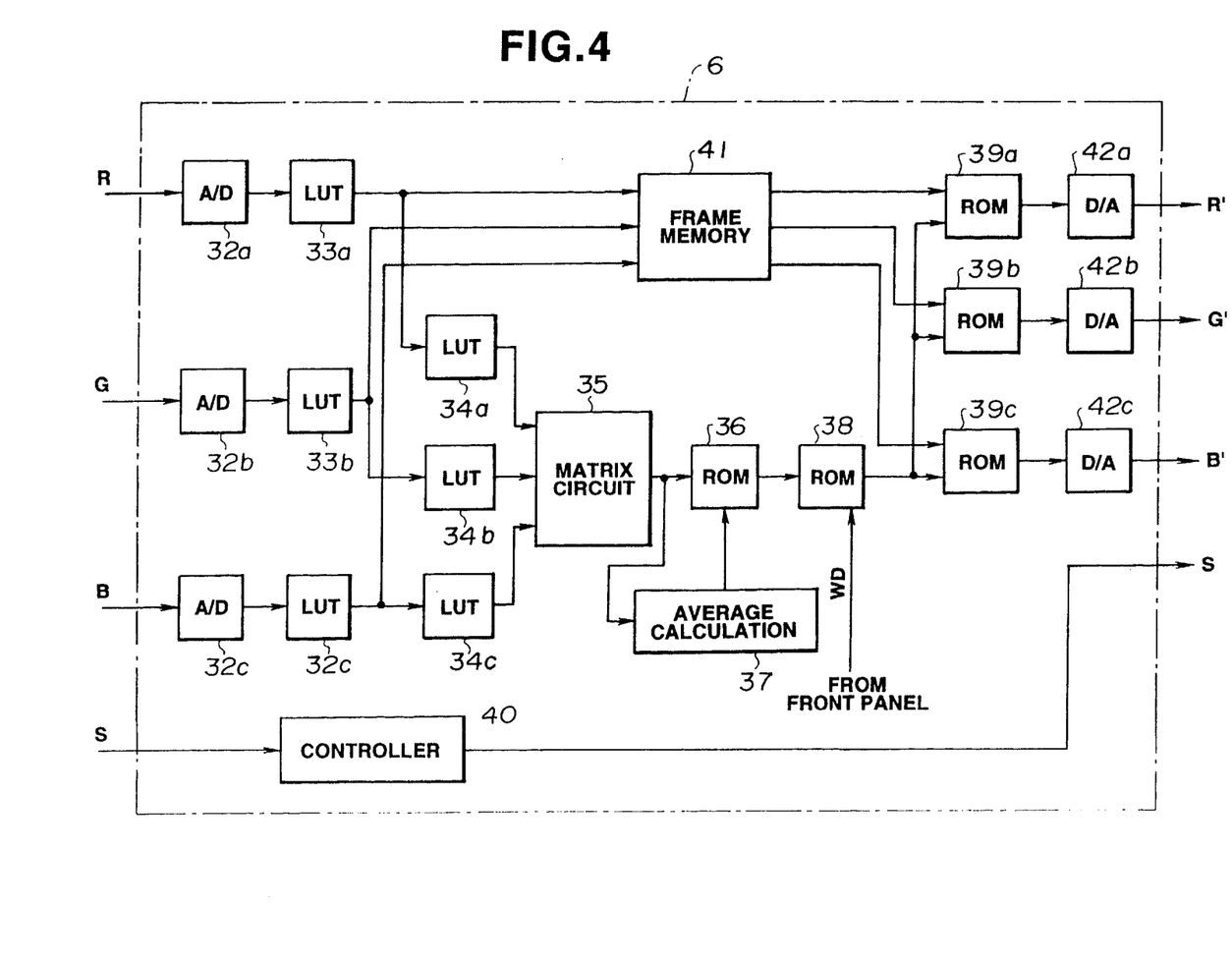
FIG. 4 is a block diagram showing an arrangement of an image emphasis unit.

FIG. 4 shows, in block diagram, an arrangement of the image emphasis unit 6. As shown in FIG. 4, the image emphasis unit 6 is provided therein with A/D converters 32a~32c for converting the three-primary-color signals R, G and B which are sent from the image recording/reproducing unit 5A, to digital signals. A controller 40 controls the incorporation of the three-primary-color signals R, G and B due to the A/D converters 32a~32c in synchronism with the input synchronous signal S.

Reverse γ correction conversion is performed with respect to the three-primary-color signals R, G and B which are converted to the digital signals, by lookup tables (hereinafter referred simply to as "LUT") 33a~33c which are provided at a later stage. The three-primary-color signals R, G and B are converted by logarithms in LUTs 34a~34c. A matrix circuit 35 for calculating an amount of hemoglobin is provided at a later stage of the LUTs 34a~34c. At a further later stage, a ROM 36 and an average calculating circuit 37 are provided.

The signal which passes through the average calculating circuit 37 is transferred to the ROM 36 so that the emphasis coefficient is calculated. The signal which passes through the ROM 36 for adjusting an amount of emphasis by data WD of the weighting coefficient which is decided by selection of an operator, through the front panel 5C. The arrangement is such that the operator operates the selective switching portion 5D of the front panel 5C to thereby variably set the weighting coefficient WD, whereby setting can be made to the order of emphasis and tone which the operator likes.

Signal lines sent from the LUTs 33a~33c are connected respectively to the ROMs 39a~39c for conversion of the emphasis image, which are provided at the later stage of the ROM 38, through a frame memory 41 for adjustment of timing. D/A converters 42a~42c are connected to a later stage of the signal lines. The analog signal which is D/A-converted is output to the image recording/reproducing unit 5A within the image filing device 5 through SW2, and is output to the monitor 4 through the switch SW1 within the video processor 3.

Figure 5:
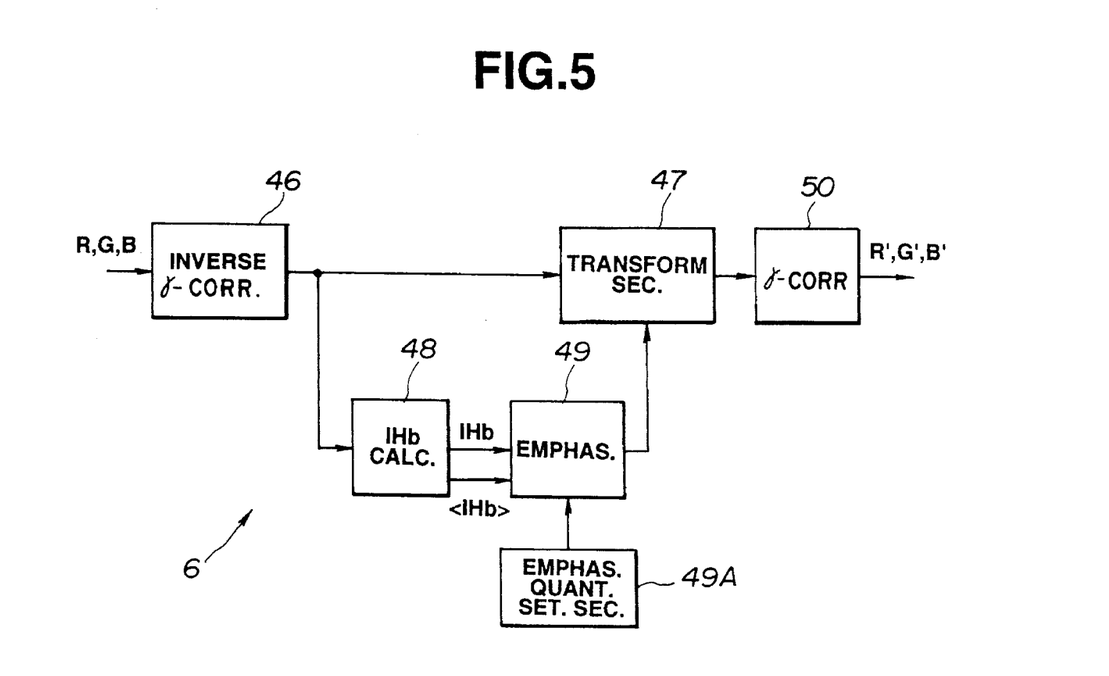
FIG. 5 is an explanatory view showing emphasis processing function due to the image emphasis unit.

The schematic arrangement of the image emphasis unit 6 illustrated in FIG. 4 is as shown in FIG. 5. The color signals R, G and B are converted to a color signal having linear characteristics by the inverse γ correcting circuit 46, thereafter, are inputted to a transform section 47, and is input to an IHb calculating portion 48. The IHb calculating portion 48 calculates IHb from the color signal for each pigment having linear characteristics.

That is, the IHb concentration distribution data are calculated. Further, an average <IHb> of the concentration is found. The concentration distribution data are generated such that the IHb is emphasized by the emphasis portion 49, with respect to an amount of shift from the average <IHb>. Subsequently, the emphasized concentration distribution data are converted to a color signal in which the IHb in the color signal is emphasized in amount of shift from the average, by the transform section 47. The color signal is output as color signals R', G' and B' having the γ characteristics, by a γ-correcting circuit 50. The emphasis portion 49 performs emphasis in accordance with emphasis-amount setting data from an emphasis-amount setting portion 49A.

The present embodiment is characterized as follows. That is, the concentration distribution data of the IHb are calculated from the original picture image as shown in FIG. 5 and, thereafter, emphasis of the concentration distribution of the IHb (emphasis of the concentration distribution with respect to shift from the average of the IHb) is performed without the fact that the original picture image is not emphasized directly by the calculated concentration distribution data of the IHb. Thereafter, conversion is made to the original picture image so as to have the emphasized concentration distribution of the IHb (replacement or substitution of the IHb of the original picture image to or for the emphasized IHb). As a result, an image in which the concentration distribution of the IHb is emphasized by the amount of shift from the average is calculated with respect to the original picture image.

Accordingly, as will be seen from the processing, the endoscope image produced by the present embodiment has characteristics of a normal endoscope image (endoscope image which is image-picked up in a visible range of R, G and B ) with respect to a majority of the normal parts having an average of the IHb. Thus, there is provided an emphasis image having the concentration distribution of the IHb such that a pigment-amount portion (a portion which is high in possibility of being abnormal) in which the IHb is shifted from the average is conspicuous.

Next, operation of the endoscope apparatus 1 provided with the first embodiment will hereunder be described. First, the electronic endoscope 2, the video processor 3, the monitor 4 and the image filing device 5 are connected to each other as shown in FIG. 1. The inserting section 7 of the electronic endoscope 2 is inserted into an organism 44. A part to be inspected 45, such as an affected or diseased part, is set to a position capable of being observed. Under the condition, the illuminating lights of the respective visible wavelength ranges of R, G and B are supplied from the light-source unit 3A illustrated in FIG. 2 to the end surface of the light guide 18 of the electronic endoscope 2 adjacent to the side at hand. The illuminating light is transferred and is output forwardly from the end surface adjacent to the forward end 12, to successively illuminate the part to be inspected 45 by the respective lights of R, G and B.

The illuminated part to be inspected 45 is imaged onto the photoelectric conversion surface of the CCD array 23 by the objective optical system 17 which is mounted on the observation window. The image signal which is photoelectrically converted, that is, an image signal corresponding to the endoscope image is output from the CCD array 23 to the signal processing circuit 3B of the video processor 3. By the signal processing circuit 3B, processing in which a standard image signal is generated is performed so that the three-primary-color signals R, G and B are generated.

The three-primary-color signals R, G and B are arranged such that, in a case where the switch SW is set to the side of a contact a, the endoscope image which is detected in the visible region is displayed. Moreover, the three-primary-color signals R, G and B are input to the image recording/reproducing unit 5A of the image filing device 5. The endoscope image data which are detected in the visible range are recorded.

In a case where reproduction is indicated and emphasis processing is indicated with respect to the endoscope image data which are recorded onto the image recording/reproducing unit 5A, inputting is made to the image emphasis unit 6, and processing as illustrated in FIG. 6 is performed.

As shown in Step S1, setting of a parameter is performed. In this case, data required for the emphasis processing such as inputting of the file name of the image data which are processed in emphasis and which are reproduced, from the keyboard portion 5C of the front panel 5B, turning-ON and -OFF of the selective switching portion 5D, or designation of the weighting coefficient WD of the emphasis from the keyboard portion 5C, are input.

Next, as shown in Step S2, the designated RBG image data are input to the image emphasis unit 6. That is, the image data of the inputted file name are read into the image emphasis unit 6 from the image recording/reproducing unit 5A.

$\gamma$ correction for linearizing the input and output characteristics of the monitor 4 is applied to the read image data. Accordingly, as shown in Step S3, inverse $\gamma$ correction is performed, and the image data are brought to linear data.

Subsequently, as shown in Step S4, calculation of the amount of hemoglobin (IHb) is performed. The amount of hemoglobin that is the functional information of the organism tissue is calculated for every pigment. Accordingly, the concentration distribution of the IHb in the RGB images is calculated.

As shown in Step S5, an average of the amount of hemoglobin corresponding to a single image plane is found with respect to effective pigments. A new amount of hemoglobin is decided for every pigment with the average serving as a reference.

In a case where a reference value such as the average of the amount of hemoglobin, is calculated, the reference value is calculated except for a portion which is considered such that the amount of hemoglobin, for example, cannot accurately be calculated (the foreign matters except for organism such as halation, a dark part, a dyeing part, forceps or the like).

Further, the weighting coefficient WD of the emphasis and the average which are input at the beginning is used to perform processing to calculate an emphasized IHB' from the IHb as shown in Step S6, that is, processing of data conversion to be converted to the emphasized IHB' concentration distribution.

After the emphasized IHb' has been calculated, the IHB' is used as shown in Step S7 to perform creation processing of the emphasis image which is turned to the RGB image data. That is, image data in which an amount of hemoglobin shifted from the average of the amount of hemoglobin is emphasized are created with respect to the image data which are inverse-$\gamma$-corrected.

The $\gamma$ correction is further performed as shown in Step S8 with respect to the emphasized image data. As shown in Step S9, the image data are output as an image file.

The image file is recorded onto the image recoding/reproducing unit 5A or is output to the display unit such as the monitor 4.

Here, the calculating method of the amount of hemoglobin and the average calculating method (Steps S4 and Step S5 in FIG. 6) will be described by the use of the flow chart in FIG. 7. It is assumed that, if the image is expressed by two-dimensional array IM (X, Y), X means an image size in an X-direction, while Y means an image size in a Y-direction. It is assumed that R(i,j) expresses an intensity level of the R-signal in a position (i,j), G(i,j) expresses an intensity level of the G-signal in a position (i,j) and IHb(i,j) expresses the amount of hemoglobin in the position (i,j). It is assumed that AVGIHb expresses the average of the amount of hemoglobin corresponding to a single image plane.

First, initial setting is performed as shown in Step S11. A variable or parameter i indicating a position in the X-direction, a variable j indicating a position in the Y-direction and AVGIHb are initialized (substitution of 0).

Then, processing in which the amount of hemoglobin of each pigment is calculated is performed by the following Steps S12–S19:

(1) Numeral in which a coefficient of 32 is multiplied to a logarithmic ratio between R(i, j) and G(i, j) is substituted into IHb(i, j) (Step S12).

(2) AVGIHb=AVGIHb+IHb(i, j) is executed (Step S13).

(3) i is counted up through one (1) (Step S14).

(4) It is judged whether or not i≧X (Step S15). If i<X, the program is returned to the processing of (1), while, if i≧X, (5) is executed.

(5) j is counted up through one (1) (Step S16).

(6) It is judged whether or not j≧Y (Step S17). If J<y, the program is returned to the processing of (1) through Step S18 of i =0, while, if J≧Y, (7) is executed.

(7) AVGIHb=AVGIHb/(X+Y) is executed (Step S19).

By the above-described steps, calculation of the amount of hemoglobin and calculation of the average are performed.

Next, the method of creating the emphasis image will be described by the use of the flow charge in FIG. 8. It is assumed that IHB'(i, j) expresses a newly decided amount of hemoglobin in the position (i, j) ∈r, ∈g and ∈b express respectively absorbency coefficients of hemoglobin in R, G and B filter bands, and ar (i, j), ag(i, j) and ab(i, j) are respective emphasis coefficients of the R, G and B images in the position (i, j).

Moreover, R'(i, j), G'(i, j) and B'(i, j) are the intensity levels of R, G and B in a position (i, j) which are newly decided.

Emphasis image creation processing is performed by the following steps:

(1) Initialization of 1 i=0 and j=0 is performed (Step S21).

(2) IHB'(i, j) is calculated (Step S22), and the details thereof will be described later.

(3) αr(i, j)=∈r·(IHb(i, j)−IHB'(i, j))/(∈g−∈r), αg(i, j)=∈g·(IHb(i, j)−IHB'(i, j))/(∈g−∈r), and αb(i, j)=∈b·(IHb(i, j)−IHb'(i, j))/(∈g−∈r) are executed (Step S23).

(4) R'(i, j)= R(i, j)·10^(αr(i, j)), G'(i, j)= G(i, j)·10^(αg(i, j)), and B' (i, j)= B(i, j)·10^(αb(i,j)), are executed (Step S24).

(5) i is counted up through one (1) (Step S25).

(6) It is judged whether or not i≧X (Step S26). If i<X, the program is returned to the processing of (1), while if i≧X, the processing of (7) is executed.

(7) j is counted up through one (1) (Step S27).

(8) It is judged whether or not j≧Y (Step S28). If j<Y, the program is returned to the processing of (2) through Step S29 of i=0, while, if j≧Y, the program proceeds to the subsequent or next Step.

By the above-described steps, the emphasis processing image data which are processed in emphasis in accordance with the amount of hemoglobin are created. Here, the equations which are used in the above-described processing of Steps will be described. These equations are all led form the Lambert-Beer's law.

It is assumed that IO is irradiating light intensity, l is a length of an optical path, c(i, j) and c'(i, j) are hemoglobin concentration in a position (i, j), and As is a correction term such as scattering or the like. Assuming that R(i, j) is changed to R'(i, j) in a case where the hemoglobin concentration of the organism is changed from c(i, j) to c'(i, j), there are provided the following equations, from the Lambert-Beer's law:

$$Log(IO/R(i, j))= \in r \cdot l \cdot c(i, j)+As \quad (1)$$

$$Log(IO/R'(i, j))= \in r \cdot l \cdot c'(i, j)+As \quad (2)$$

By the above-described equations (1) and (2), there is provided the following equation (3):

$$R'(i, j)= R(i, j) \cdot 10^{(\in r \cdot l \cdot (c(i, j)-c'(i, j)))} \quad (3)$$

Here, the relationship is as follows:

$$IHb(i, j)=(\in g-\in r) \cdot l \cdot c(i, j) \quad (4)$$

$$IHb'(i, j)=(\in g-\in r) \cdot l \cdot c'(i, j) \quad (5)$$

Accordingly, from the equations (4) and (5), there is provided the following equation:

$$R'(i, j)=R(i, j) \cdot 10^{(\in r \cdot r(IHb(i, j)-IHb'(i, j))/(\in g-\in r)} \quad (6)$$

Similarly to the equation (6), there are provided the following equations:

$$G'(i, j)=G(i, j) \cdot 10^{(\in g \cdot (IHb(i, j)-IHb'(i, j))/(\in g-\in r)} \quad (7)$$

$$B'(i, j)=B(i, j) \cdot 10^{(\in b \cdot (IHb(i, j)-IHb'(i, j))/(\in g-\in r)} \quad (8)$$

In this manner, if the new amount of hemoglobin IHb' is decided, there is provided an image in which the amount of hemoglobin IHb(i, j) is converted to IHb'(i, j) in the original picture image. That is, if the amount of hemoglobin in the position (i, j) is calculated from the newly decided image, there is provided IHb'(i, j).

Furthermore, a method of deciding the amount of hemoglobin IHb'(i, j) is such that a pigment higher in value than the average AVGIHb of the hemoglobin within the image is converted to an amount of hemoglobin of a further higher value, while a pigment lower in value than the average AVGIHb is converted to am amount of hemoglobin of a further lower value. If K is a variable coefficient, the following equation is provided:

$$IHb'(i, j)=(IHb(i, j)-AVGIHb) \cdot K+AVGIHb \quad (9)$$

Here, the average is used as a reference value. However, a fixed value such as the result that the amount of hemoglobin in the organism tissue is taken as data by prior experiments or the like may be used. Further, setting may be made such that each value IHb'(i, j) is larger than the amount of hemoglobin of the original picture image.

Operation of the image emphasis will next be described with reference to the arrangement in FIG. 4. A signal sent from the image recording/reproducing unit 5A is converted to a digital signal by the A/D converters 32a–32c. The inverse γ correction conversion is performed with respect to the RGB signals which are converted to the digital signals, by the LUTs 33a–33c, and is sent to the frame memory 41 and the LUTs 34a–34c.

Figure 7:
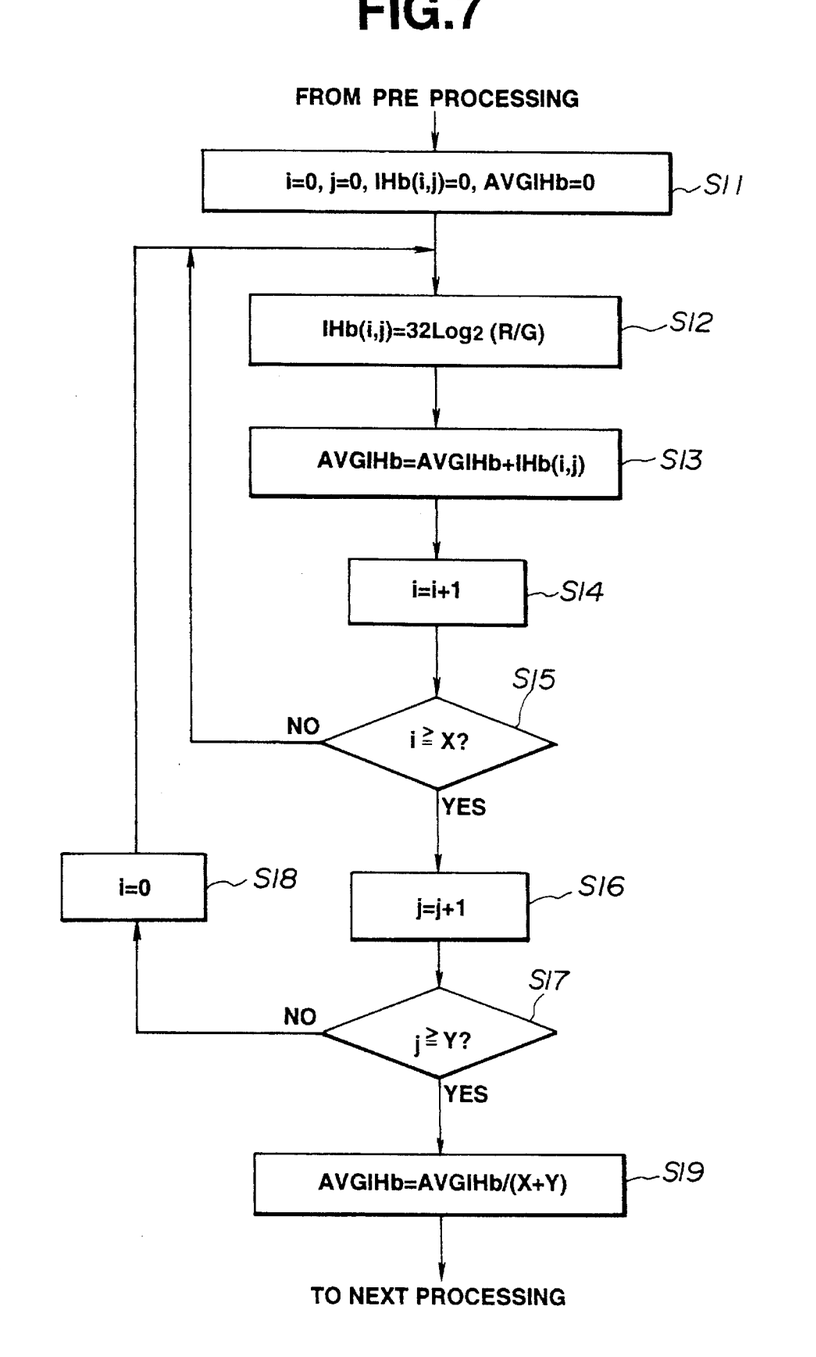
FIG. 7 is a flow chart of hemoglobin-amount calculation processing and average calculation processing.

In the LUTs 34a–34c, logarithmic conversion that becomes preprocessing in which Step S12 in the hemoglobin calculating processing in FIG. 7 is performed. After the color signals R, G and B have been converted in logarithm, processing (or Step S4 in FIG. 6) corresponding to Step S12 in the hemoglobin calculating processing in FIG. 7 is performed at the matrix circuit 35, to calculate the amount of hemoglobin IHb.

The calculated amount of pigment is sent to the average calculating circuit 37. In the average calculating circuit 37, processing corresponding to step S19 in FIG. 7 is performed, to calculate average AVGIHb data of the amount of hemoglobin. The calculated AVGIHb data and the pigment-amount data outputted from the matrix circuit 35 are sent to the ROM 36. In the ROM 36, the emphasis treatment in step S6 in FIG. 6, that is, IHb conversion processing to calculate the emphasis-processed IHb' (or step S22 in FIG. 8) is performed.

Figure 8:
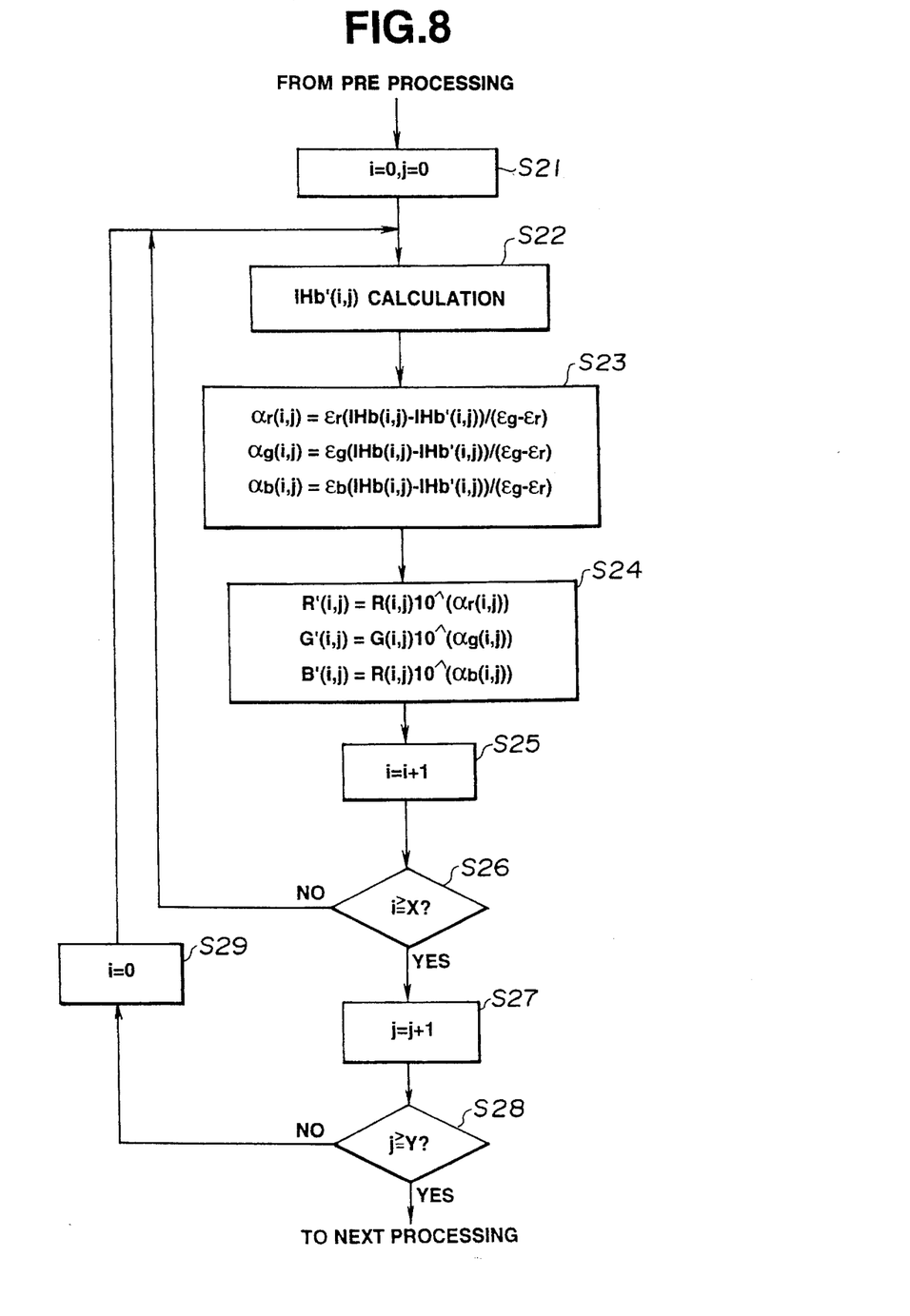
FIG. 8 is a flow chart of emphasis image creating processing.

Data conversion corresponding to step S23 in FIG. 8 is performed by the ROM 38 with respect to the IHb' which is calculated by the ROM 36, and the IHb' is transmitted to the ROMs 39a–39c. In the ROMs 39a–39c, data conversion corresponding to Step S7 in FIG. 6 or Step 24 in FIG. 8 is performed by the RGB signals which are adjusted in timing by the frame memory 41 and aa, ab and ac which are calculated by the ROM 38.

Furthermore, γ correction is also performed by the ROMs 39a–39c. The R', G' and B' image signals which are created here are converted to analog signals by the D/A converts 42a –42c and, thereafter, are recorded by the filing portion 5A. The R', G' and B' image signals are displayed on the monitor 4 through the contact b of the switch SW1 within the video processor 3.

Further, in the present embodiment, the ROM and the matrix circuit are used to perform conversion of the data. However, a field programmable gate array may be used in place of the ROM and the matrix circuit to perform processing.

According to the present embodiment, it is possible to express more effectively and naturally the emphasis of a part in which a bloodstream condition is changed from a peripheral mucous membrane or the like, such as a blood vessel portion, a diseased or affected part or the like.

If the present embodiment is further described, the present embodiment has the following merits. In the present embodiment, the concentration distribution of IHb is calculated with respect to the endoscope image which is detected in the visible region, the average thereof is calculated, and the emphasis processing which is converted to the endoscope image in which each IHb is substituted so that each IHb is enlarged by the amount of shift from the average is performed. Accordingly, the image is brought to an image in which a diseased part of an initial condition such as erythrogenesis in which IHb is slightly shifted from the average is distinguished in tone from the average portion (that is, most normal part portions). For this reason, the diseased part can be identified at an early stage, the possibility that an operator overlooks the diseased part can be reduced, and a discovery of the diseased part is facilitated. Thus, it is possible to reduce the burden of the operator.

Moreover, since the diseased part can be identified at an early stage, medical treatment can also be facilitated.

Furthermore, since the average portion is not emphasized, the normal part portion which corresponds to the average portion is the same as the one which is detected in the normal visible region. Accordingly, it is possible to provide an emphasized endoscope image which is suitable for diagnosis having no feeling of physical disorder.

That is, only a portion having IHb which is changed from the IHb of the normal part is emphasized with respect to a normal endoscope image.

Accordingly, the present embodiment is capable of identifying the diseased part from only the image processed in emphasis, without comparison with the normal endoscope image. Thus, the present embodiment can provide a very effective image in a case of being diagnosed.

Further, the first embodiment calculates the IHb from the endoscope image which is image-picked up by normal visibility so that there can be produced an image having the above-described merits. That is, it is possible to produce an emphasis image suitable for diagnosis having the above-described merits, by addition of the image emphasis unit 6, also with respect to the endoscope image which has already been recorded on the existing endoscope image recording device or the like, without the use of an image which is detected in a special or specific wavelength region. Accordingly, it is possible to provide an auxiliary diagnosis or device which has a wide range of applications.

By the way, the above-described embodiment is an embodiment regarding an image which has no affection such as a dyeing pigment or the like. Since, however, an image of a portion which is dyed by a dyeing pigment such as methylene blue or the like is et such that the amount of hemoglobin is IHb=0, the image of a portion which is dyed by a dyeing pigment is emphasized by an emphasis coefficient similar to that of a portion in which IHb does not exist.

Moreover, a conversion equation which converges the emphasized amount of hemoglobin to 0 (zero) may be used. Furthermore, since the amount of hemoglobin IHb of the portion which is dyed by methylene blue becomes a negative value, if the emphasis processing performed as it is, the emphasized image is produced also with respect to the dyeing. Further, in the first embodiment, calculation is performed such that the absorption coefficients in the wavelength regions ofG and B of the hemoglobin are separated from each other. However, the calculation may be performed as the absorption coefficients in the wavelength regions ofG and B of the hemoglobin being simply the same or identical to each other.

As described above, according to the first embodiment, it is possible to emphasize a portion in which the bloodstream condition is changed from the peripheral mucous membrane, such as the blood vessel portion, the diseased portion or the like. Thus, it is possible to produce the image which is easy to easily perform identification of the diseased part. Further, it is possible to perform expression naturally.

Accordingly, the first embodiment is effective in a case where the bloodstream condition is diagnosed, and is also effective for preventing the diseased part from being overlooked.

Figure 9:
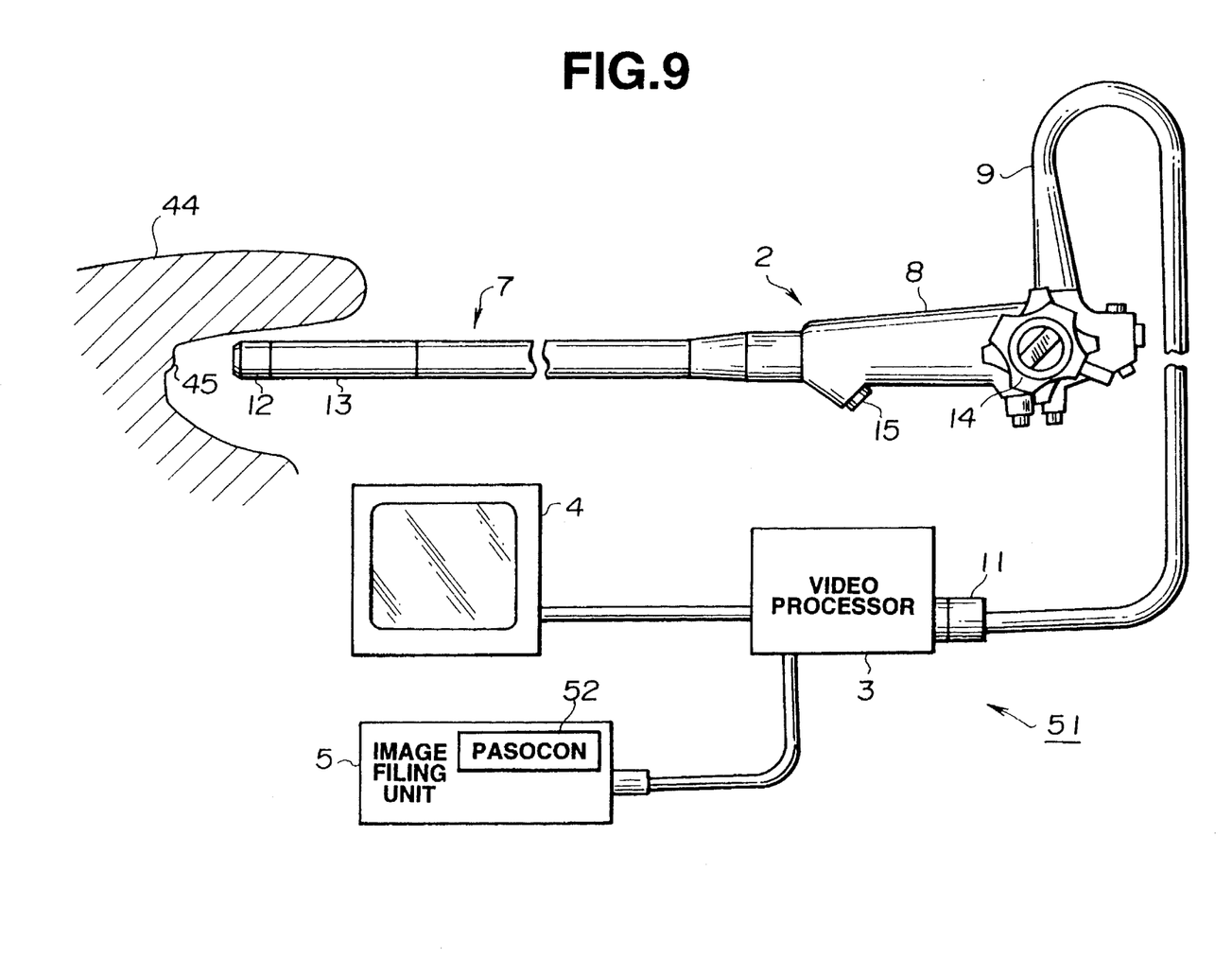
FIG. 9 is a side elevational view showing an entire endoscope apparatus which is provided with a modification of the first embodiment.

FIG. 9 shows an endoscope apparatus 51 according to a modification of the first embodiment. The modification is arranged such that the image filling device 5 does not incorporate therein the image emphasis unit 6, but incorporates therein a person computer (pasocon) 52 for performing the emphasis processing shown in FIG. 6 (or the emphasis processing illustrated in FIGS. 7 and 8) by software. Operation of the modification is the same as that described with reference to FIG. 6 (or FIGS. 7 and 8) and, accordingly, the description thereof will be omitted.

The modification is such that it takes much more time than the first embodiment to produce the endoscope image which is processed in emphasis, but can produce similar advantages. Meanwhile, in the first embodiment it is possible to produce the endoscope image processed in emphasis, substantially with real time.

Moreover, the present invention should not be limited to the electronic endoscope having the solid-state image pickup device at the forward end of the inserting section, but is applicable to an endoscope which is so used that an exterior television camera having a solid-state image pickup device such as a CCD or the like is connected to an ocular portion of an endoscope which is capable of performing naked-eye observation such as a fiber scope, a rigid mirror or the like, or with replacement to the ocular portion.

Furthermore, the arrangement may be a system in which processing circuits of a simultaneous or concurrent system and a surface sequential system are provided within the camera control unit, and the illuminating light of the light source is changed or modified, whereby the normal color image and the infrared observation are made possible by the surface sequential scope, to perform normal, fluorescent and infrared observation.

What is claimed is:

1. An endoscope apparatus comprising:

an endoscope provided with an inserting section insertable into an organism, illuminating-light outputting means for outputting illuminating light to a part to be inspected within said organism, from a side of a forward end of said inserting section, and an image pickup device for photoelectrically converting an optical image in response to an objective optical system which is provided on the side of the forward end of said inserting section;

signal processing means for performing signal processing for displaying an image of said part to be inspected, from an output signal output from said image pickup device;

pigment-amount calculating means for calculating an amount of pigment with respect to said part to be inspected, from said output signal from said image pickup device, wherein said pigment-amount calculating means includes concentration distribution calculating means for calculating amounts of pigments of respective parts of said endoscope image from said image signal, to calculate a pigment concentration distribution with respect to said endoscope image;

emphasis means for performing emphasis processing on said image in response to the amount of pigment which is calculated by said pigment-amount calculating means, wherein said emphasis means has concentration distribution enlarging means for enlarging an amount of shift from a reference value of the concentration distribution of said amount of pigment which is calculated by said concentration distribution calculating means, and wherein said emphasis means generates said emphasis processing image which has the concentration distribution of the amount of pigment which is enlarged by said concentration distribution enlarging means; and display means for displaying an emphasis processed image which is processed in emphasis by said emphasis means, wherein said emphasis processed image contains said pigment concentration distribution which is emphasized by the amount of shift from said reference value calculated with respect to an original picture image contained in said output signal, and wherein said reference value is one of an average of said amounts of pigment and the amount of pigment which is distributed with a greatest frequency.

2. An endoscope apparatus according to claim 1, wherein said emphasis means has concentration distribution emphasis means for emphasizing the concentration distribution of said amount of pigment which is calculated by said concentration distribution calculating means, and wherein said emphasis means generates said emphasis processing image having the concentration distribution of the amount of pigment which is emphasized by said concentration distribution emphasis means.

3. An endoscope apparatus according to claim 1, wherein said illuminating-light outputting means outputs the illuminating light of a visible region.

4. An endoscope apparatus according to claim 1, wherein said illuminating-light outputting means outputs the illuminating light corresponding to a wavelength region which is absorbed by said amount of pigment.

5. An endoscope apparatus according to claim 1, wherein said illuminating-light outputting means outputs successively the illuminating lights of a plurality of wavelength regions.

6. An image processing unit for an endoscope, comprising:

pigment-amount calculating means for calculating an amount of pigment with respect to an image signal corresponding to an endoscope image which is produced by the use of the endoscope, wherein said pigment-amount calculating means includes concentration distribution calculating means for calculating amounts of pigments with respect to respective parts of said endoscope image, from said image signal to calculate a pigment concentration distribution with respect to said endoscope image, and wherein said pigment-amount calculating means includes average calculating means for calculating an average of the amount of pigment which is contained in said endoscope image;

emphasis means for performing emphasis processing to said image signal, in response to the amount of pigment which is calculated by said pigment-amount calculating means, wherein said emphasis means includes concentration distribution enlarging means for enlarging an amount of shift from a reference value of the concentration distribution of said amount of pigment which is calculated by said concentration distribution calculating means, and wherein said emphasis means generates said emphasis processing image having the concentration distribution of the amount of pigment which is enlarged by said concentration distribution enlarging means, and wherein said emphasis means performs emphasis processing with said average used as the reference value; and display means for displaying an emphasis processing image which is processed in emphasis by said emphasis means, wherein said emphasis processed image contains said pigment concentration distribution which is emphasized by the amount of shift from said reference value calculated with respect to an original picture image contained in said output signal.

7. An endoscope apparatus according to claim 6, wherein said emphasis means has concentration distribution emphasis means for emphasizing concentration distribution of said amount of pigment which is calculated by said concentration distribution calculating means, and wherein said emphasis means generates said emphasis processed image having concentration distribution of the amount of pigment which is emphasized by said concentration distribution emphasis means.

8. An endoscope apparatus according to claim 6, wherein said reference value is one of an average of said amount of pigment and a most dominant value of the amount of pigment in which the amount of pigment is distributed with the greatest frequency.

9. An endoscope apparatus according to claim 6, including emphasis-amount setting means for optionally setting an amount of emphasis which is processed in emphasis by said emphasis means.

10. An endoscope apparatus according to claim 6, including emphasis processing image recording means for recording said emphasis processed image.

11. An endoscope apparatus according to claim 6, wherein said emphasis means processes in emphasis an amount of shift from a reference value with respect to various parts of the image signals corresponding respectively to various parts of said endoscope image by utilizing said amount of pigment which is calculated with respect to various parts of said endoscope image.

12. An endoscope apparatus according to claim 6, wherein said emphasis means has characteristics which exponentially emphasize an amount of shift from said reference value.

13. An endoscope apparatus according to claim 6, wherein said pigment-amount calculating means has reference-value calculating means for calculating a reference value in a case of being emphasized by said emphasis means.

14. An endoscope apparatus according to claim 6, wherein said emphasis means performs emphasis processing with respect to a plurality of color image components in a color endoscope image which is detected in a visible region.

15. An endoscope apparatus according to claim 6, wherein said endoscope image is a color image which is image-picked up under the illuminating light of a visible region, and wherein said pigment-amount calculating means calculates said amount of pigment in response to said color image.

16. An endoscope apparatus according to claim 6, wherein said pigment-amount calculating means includes a correction circuit for performing correction for bringing input and output characteristics of said image signal inputted to linearity.

17. An endoscope apparatus according to claim 14, wherein said plurality of color image components are three-primary-color image components of R, G and B.

18. An endoscope apparatus according to claim 10, wherein said absorbency pigment is at least one of an ICG, a hemoglobin pigment and a hemoglobin pigment in which saturated oxygens are coupled to each other.

19. A method of emphasizing an endoscope image, comprising:

a pigment-amount calculating step of calculating an amount of pigment contained in an endoscope image, from an image signal corresponding to the endoscope image which is produced by the use of an endoscope, wherein said pigment amount calculating step includes a concentration distribution calculating step of calculating amounts of pigments at respective various parts of said endoscope image from said image signal, to calculate a pigment concentration distribution with respect to said endoscope image;

a reference pigment-amount calculating step of calculating a reference amount of pigment, wherein said reference amount of pigment is one of an average of said amounts of pigments and the amount of pigment which is distributed with a greatest frequency;

an emphasis processed image signal generating step of generating an emphasis processed image signal in which emphasis processing is applied to said image signal, on the basis of said amount of pigment which is calculated in said pigment-amount calculating step, wherein said emphasis processed image signal generating step replaces various amounts of pigments in said endoscope image such that an amount of shift from a reference amount of pigment is enlarged, to thereby generate said emphasis processed image; and a display step of displaying said emphasis processed image signal wherein the emphasis processed image signal contains the pigment concentration distribution which is emphasized by the amount of shift from said reference value calculated in said reference value calculation step with respect to an original picture image contained in said image signal.

20. A method of emphasizing an endoscope image, according to claim 19, wherein said parameter setting step includes an emphasis-amount setting step of setting proportion of an emphasis amount of emphasis.

21. A method of emphasizing an endoscope image, according to claim 19, including a recording step of recording said emphasis processing image signal by a recording unit.

22. A method of emphasizing an endoscope image, according to claim 19, wherein said pigment-amount calculating step performs operation to calculate said amount of pigment only from said image signal corresponding to said endoscope image which is image-picked up in a visible region.

* * * * *